(12) United States Patent
Spiro

(10) Patent No.: US 8,910,318 B2
(45) Date of Patent: Dec. 16, 2014

(54) INDUCED DRAFT ANTI FOG DEVICE FOR GOGGLES

(76) Inventor: Mark Spiro, Broad Brook, CT (US)

( * ) Notice: Subject to any disclaimer, the term of this patent is extended or adjusted under 35 U.S.C. 154(b) by 423 days.

(21) Appl. No.: 13/078,689

(22) Filed: Apr. 1, 2011

(65) Prior Publication Data

US 2012/0246808 A1 Oct. 4, 2012

(51) Int. Cl.
*A61F 9/02* (2006.01)
*G02B 27/00* (2006.01)
*A42B 3/24* (2006.01)

(52) U.S. Cl.
CPC .......... *G02B 27/0006* (2013.01); *A61F 9/028* (2013.01); *A42B 3/24* (2013.01)
USPC .......................................... 2/436; 128/201.15

(58) Field of Classification Search
CPC ................................ A61F 9/028; G02C 11/08
USPC ................................ 2/436–438, 8.6; 128/201.15
See application file for complete search history.

(56) References Cited

U.S. PATENT DOCUMENTS

| | | | |
|---|---|---|---|
| 1,354,433 A * | 9/1920 | De-Felice | 2/435 |
| 1,871,534 A * | 8/1932 | Kimball | 2/436 |
| 2,099,464 A * | 11/1937 | Bruner et al. | 2/436 |
| 2,526,737 A | 10/1950 | Farina | |
| 2,539,284 A * | 1/1951 | Thomas | 2/436 |
| 2,810,386 A * | 10/1957 | Reed | 128/201.15 |
| 3,231,897 A * | 2/1966 | Woolfolk, Sr. | 2/438 |
| 3,825,953 A | 7/1974 | Hunter | |
| 4,150,443 A | 4/1979 | McNeilly | |
| 4,293,757 A * | 10/1981 | Niemi | 219/147 |
| 4,443,893 A | 4/1984 | Yamamoto | |
| 5,452,480 A | 9/1995 | Ryden | |
| 5,966,746 A | 10/1999 | Reedy et al. | |
| 6,049,917 A | 4/2000 | Ryden | |
| 6,704,944 B2 | 3/2004 | Kawainshi et al. | |
| 6,896,366 B2 | 5/2005 | Rice et al. | |

FOREIGN PATENT DOCUMENTS

| | | |
|---|---|---|
| AT | 387904 | 4/1989 |
| DE | 19645432 | 5/1998 |
| GB | 2.330.916 | 5/1999 |

\* cited by examiner

*Primary Examiner* — Clinton T Ostrup
*Assistant Examiner* — Andrew W Sutton
(74) *Attorney, Agent, or Firm* — Michael I. Kroll

(57) ABSTRACT

An induced draft anti-fog system for goggles and similar optical devices having an air tight goggle with ports, fixedly attached to a hollow elastomeric conduit. Said hollow conduit having an intake port and exhaust fan. The exhaust fan has an on/off switch in communication with two battery packs. When the fan is in operation air is drawn into the intake port and circulated into the goggle housing thereby defogging the goggle lens and then is circulated out through the fan.

10 Claims, 8 Drawing Sheets

INDUCED DRAFT ANTI FOG DEVICE FOR GOGGLES

BACKGROUND OF THE INVENTION

1. Field of the Invention

Figure 1:
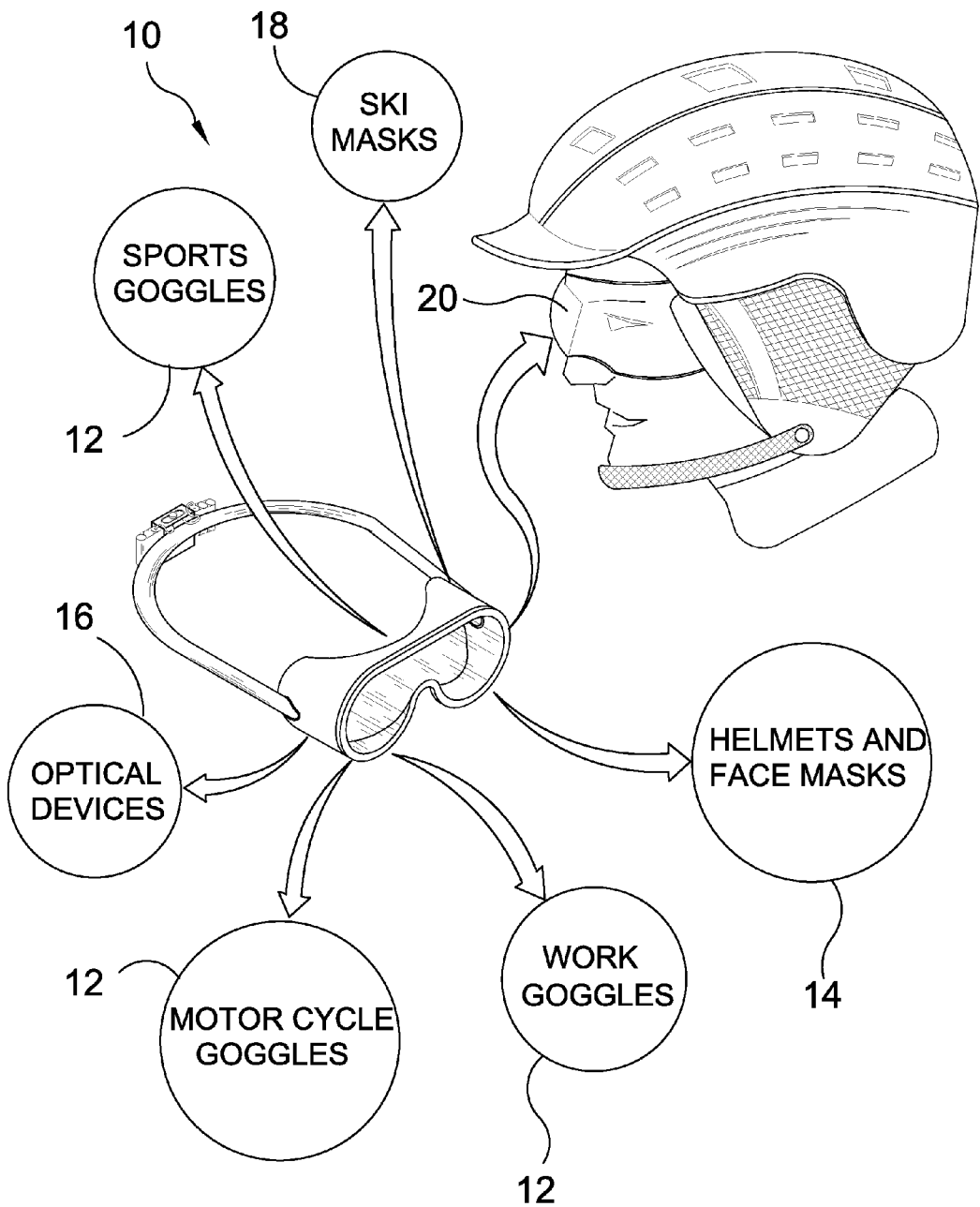

The present invention relates generally to anti-fog systems and, more specifically, to an induced draft anti-fog device for goggles and similar optical lenses having an air tight goggle with ports, fixedly attached to a hollow elastomeric conduit. Said hollow conduit having an intake port and exhaust fan. Said exhaust fan having an on/off switch in communication with two battery packs. When fan is in an on position, air is drawn into the intake port and circulated to the goggle, defogging the goggle lens and circulated out the fan.

2. Description of the Prior Art

There are other goggle device designed for anti-fogging. While these devices may be suitable for the purposes for which they where designed, they would not be as suitable for the purposes of the present invention as heretofore described.

It is thus desirable to provide an anti-fog system for goggled having a plurality of apertures with conduit having terminal ends within the goggle housing.

It is further desirable to provide an ant-fog system for goggle having a fan for circulating ambient air across the goggle lens portion.

SUMMARY OF THE PRESENT INVENTION

A primary object of the present invention is to provide anti-fig system for goggles.

Another object of the present invention is to provide an anti-fog system for goggles having a goggle portion and a strap portion.

Yet another object of the present invention is to provide an anti-fog system for goggles wherein said goggle portion has a housing portion and a lens portion.

Still yet another object of the present invention is to provide an anti-fog system for goggles wherein said goggle housing portion has at least one aperture therein for moving air in and out of said housing portion.

A further object of the present invention is to provide an anti-fog system for goggles wherein said goggle housing portion has a plurality of apertures therein for moving air in and out of said housing portion.

A yet further object of the present invention is to provide an anti-fog system for goggles wherein said goggle housing portion has a plurality of apertures within opposing sides of said housing portion thereby moving air across the lens portion preventing them from fogging up.

A still yet further object of the present invention is to provide an anti-fog system for goggles wherein said goggle housing apertures are in conduit communication with a port providing ambient air to said goggle housing portion.

An additional object of the present invention is to provide an anti-fog system for goggles wherein the goggle housing portion has a strap for holding said goggles to a user face.

Another object of the present invention is to provide an anti-fog system for goggles wherein said conduit is preferably an elastomeric or polymeric conduit.

Yet another object of the present invention is to provide an anti-fog system for goggles wherein the elastomeric or polymeric conduit forms said strap.

Still yet another object of the present invention is to provide an anti-fog system for goggles wherein said conduit has an aperture approximate the rear providing a source of ambient air.

A further object of the present invention is to provide an anti-fog system for goggles further comprising a fan for accelerating air movement into or out of said conduit.

A yet further object of the present invention is to provide an anti-fog system for goggles further comprising a power source for energizing said fan.

A still yet further object of the present invention is to provide an anti-fog system for goggles having a power source receptacle for mounting a plurality of batteries therein.

An additional object of the present invention is to provide an anti-fog system for goggles having a hood for said fan to keep water and dirt from entering the ambient air conduit.

Another object of the present invention is to provide an anti-fog system for goggles having a filter material positioned within the ambient air conduit.

Additional objects of the present invention will appear as the description proceeds.

The present invention overcomes the shortcomings of the prior art by providing an induced draft anti-fog system for goggles and similar optical devices having an air tight goggle with ports, fixedly attached to a hollow elastomeric conduit. Said hollow conduit having an intake port and exhaust fan. Said exhaust fan having an on/off switch in communication with two battery packs. When fan is in an on position, air is drawn into the intake port and circulated to the goggle, defogging the goggle lens and circulated out the fan.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

Figure 2:
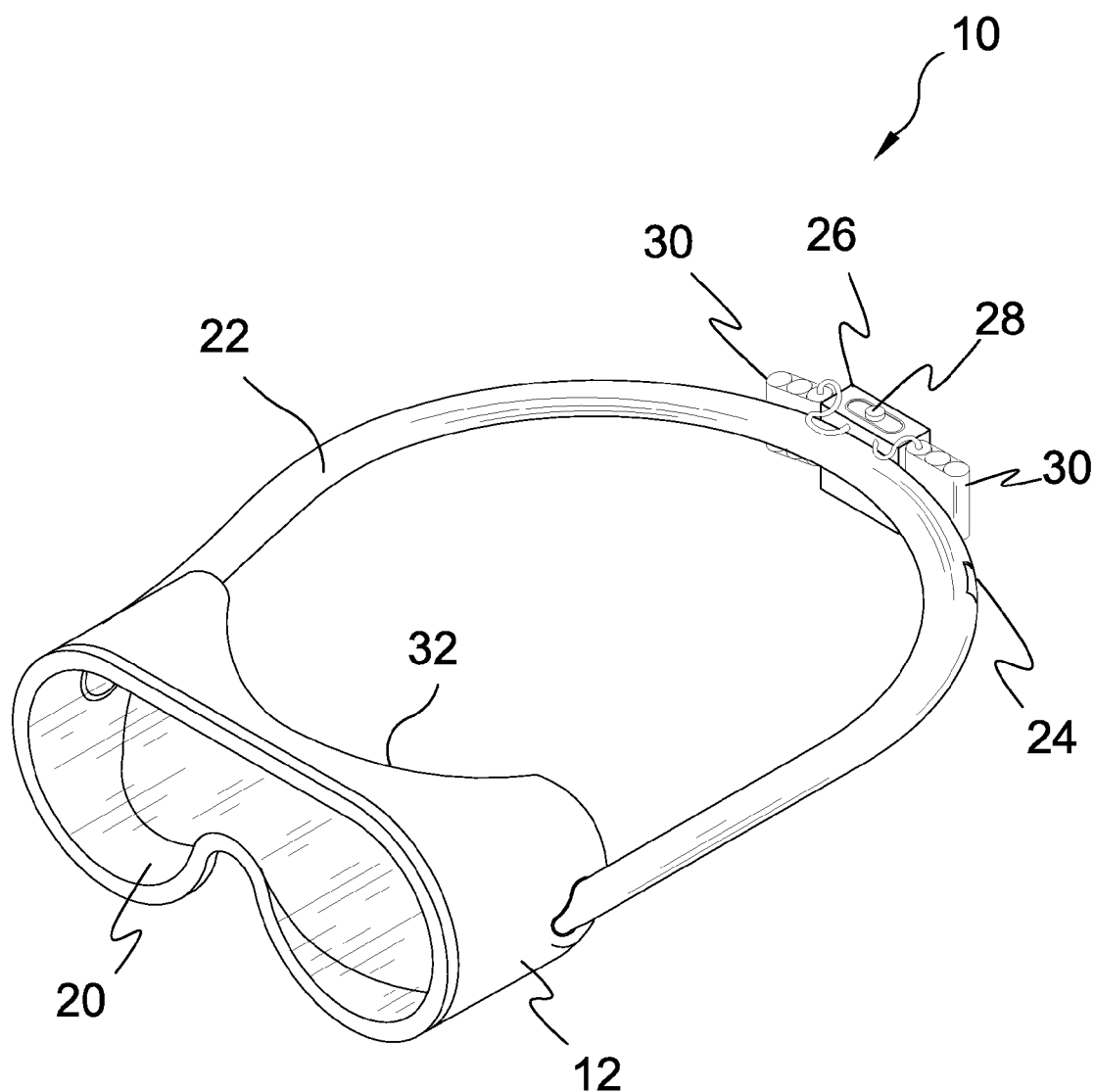
Figure 3:
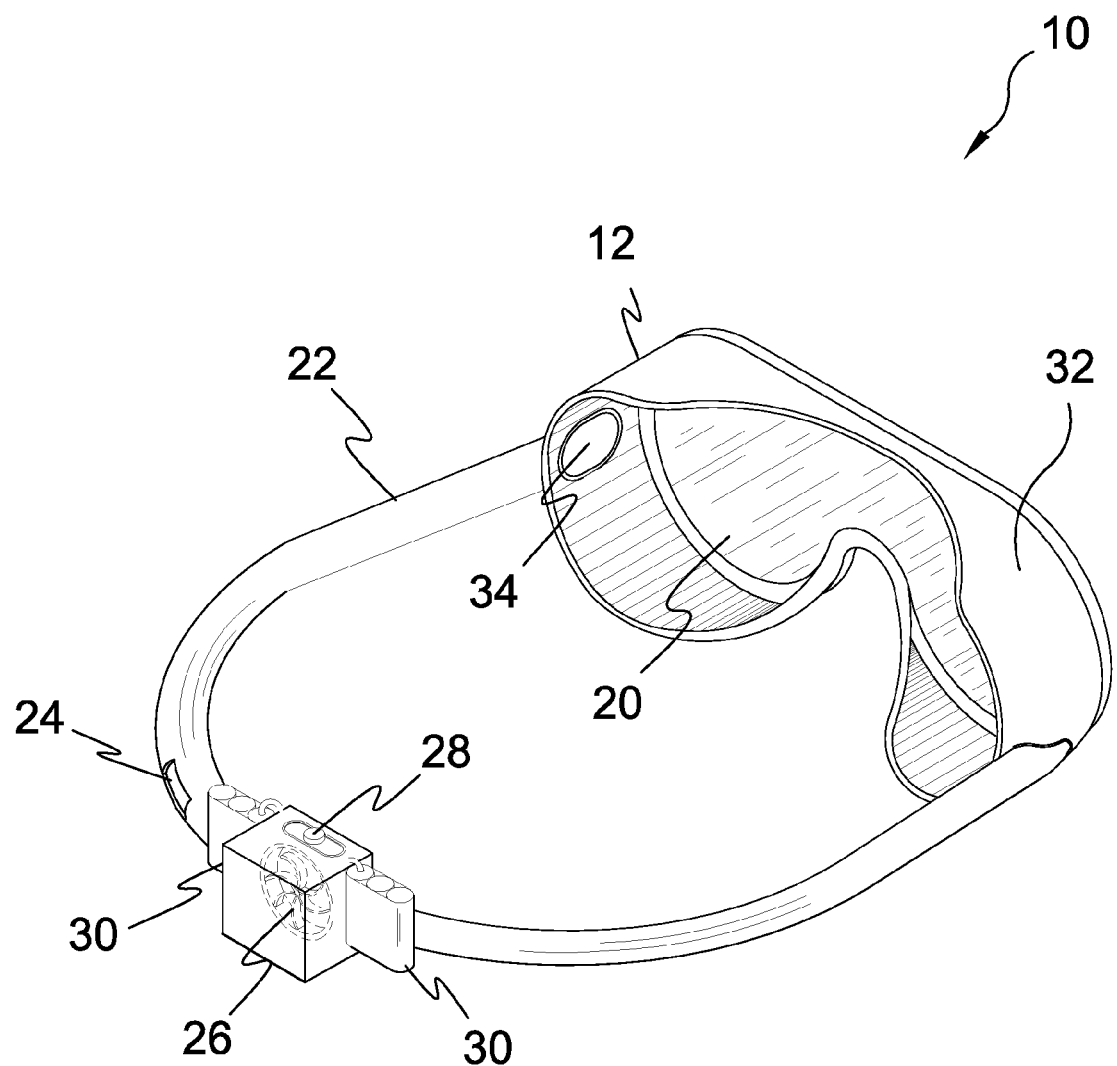
Figure 4:
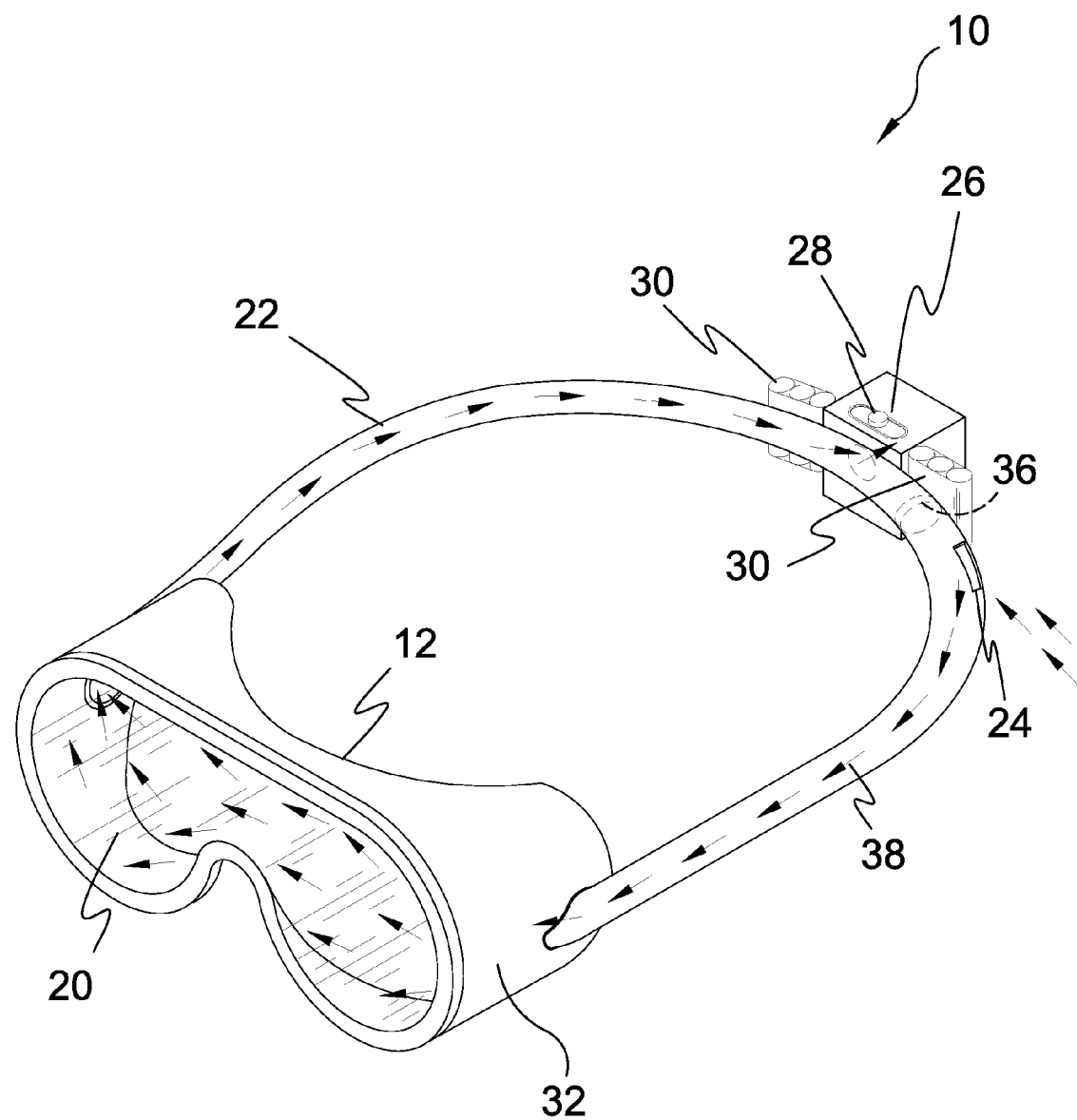
Figure 5:
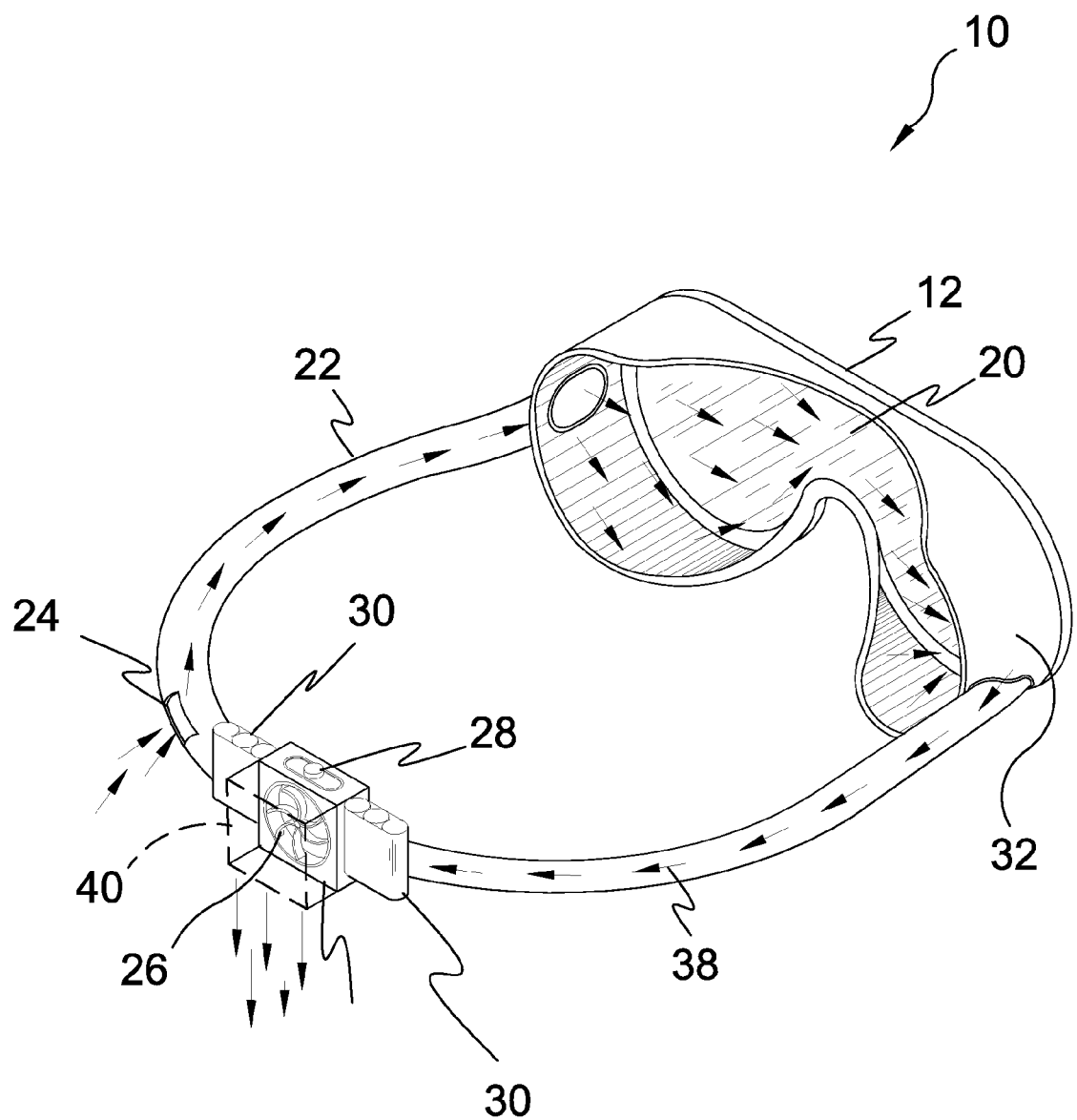
Figure 6:
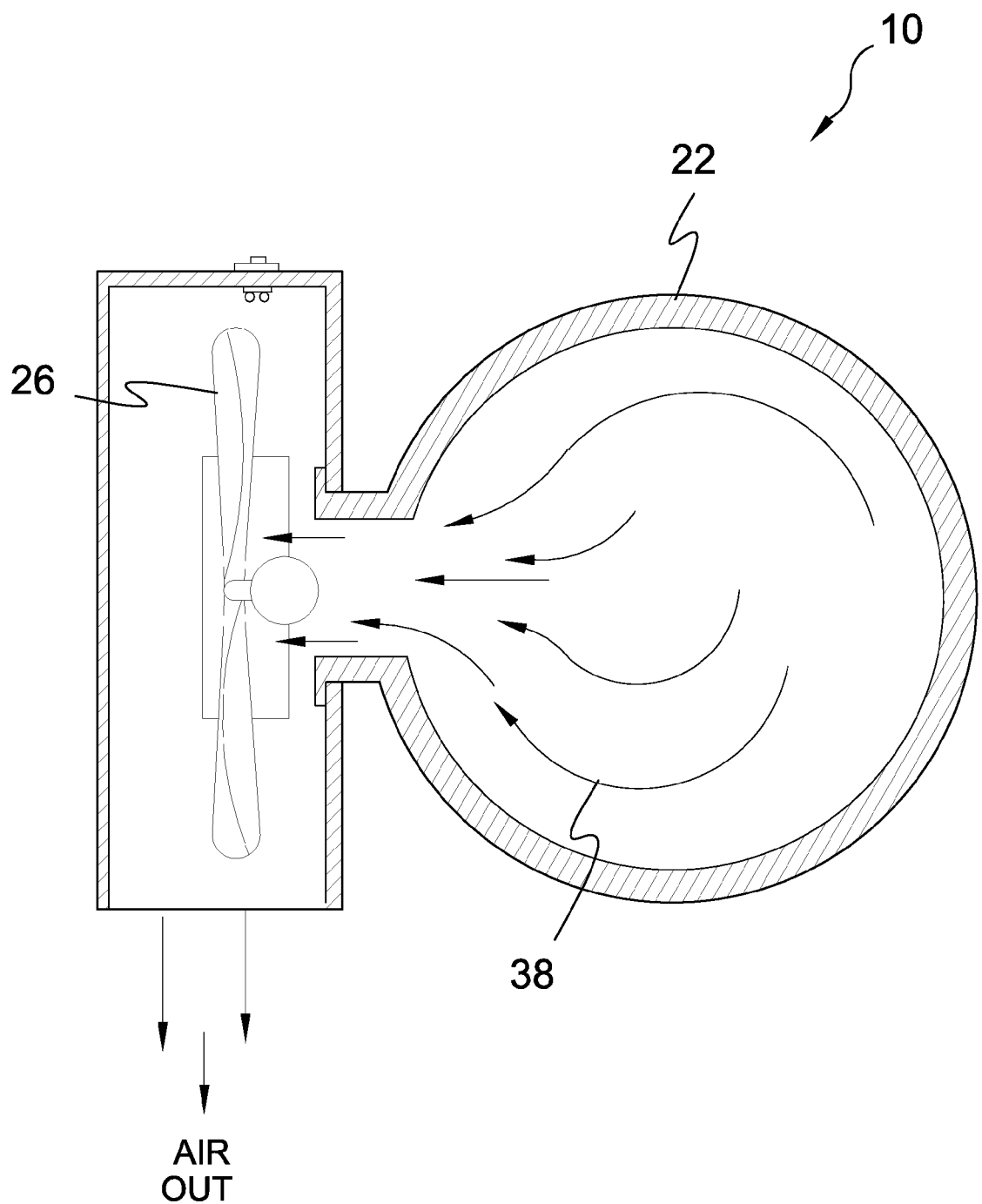
Figure 7:
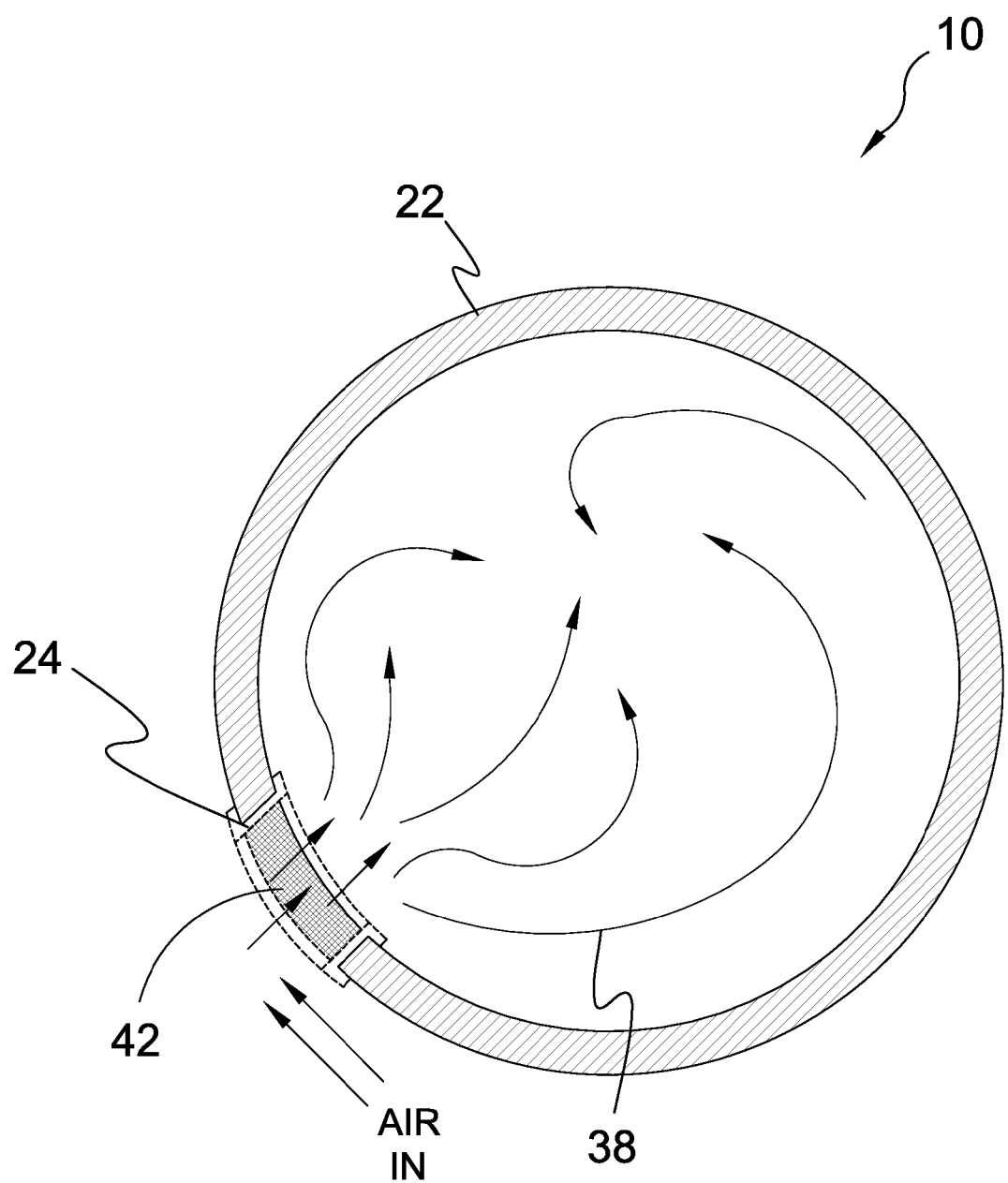
Figure 8:
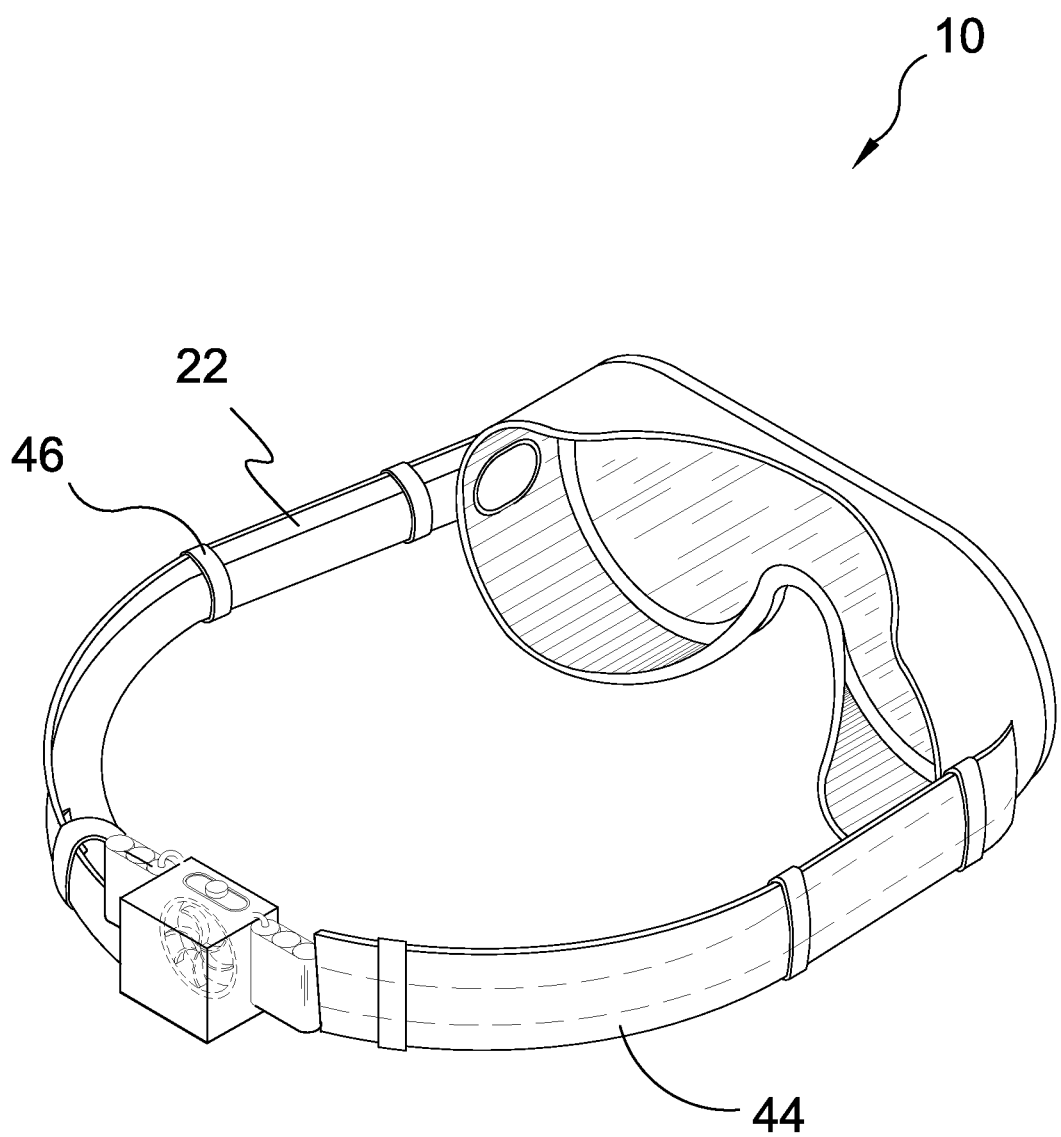

In order that the invention may be more fully understood, it will now be described, by way of example, with reference to the accompanying drawing in which:

FIG. 1 is an illustrative view of the present inventions uses.
FIG. 2 is a front perspective view of the present invention.
FIG. 3 is a rear perspective view of the present invention.
FIG. 4 is a frontal perspective view of the present invention.
FIG. 5 is a rear perspective view of the present invention.
FIG. 6 is a sectional view of the present invention.
FIG. 7 is a sectional view of the present invention.
FIG. 8 is an additional element of the present invention.

DESCRIPTION OF THE REFERENCED NUMERALS

Turning now descriptively to the drawings, in which similar reference characters denote similar elements throughout the several views, the figures illustrate the Induced Draft Anti-Fog System for Goggles of the present invention. With regard to the reference numerals used, the following numbering is used throughout the various drawing figures.

10 induced Draft Anti-Fog System for Goggles of the present invention
12 goggles
14 face shield
16 optical device
18 ski goggles
20 goggle lens
22 air circulation conduit
24 air intake port
26 exhaust fan
28 on/off switch
30 battery
32 housing of 12
34 air aperture
36 air barrier
38 air circulation
40 hood
42 air intake filter
44 elastic strap
46 loop of 44

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

FIG. 1 is an illustrative view of the present inventions uses. The present invention is an induced draft anti-fog system for goggles 10 and similar optical devices. The present invention could be utilized with goggles 12, helmets and face shields 14, optical devices 16 and ski goggles 18 that allows air to circulate through a hollow elastomeric conduit across the goggle lens 20 thereby defogging said lens 20.

FIG. 2 is a front perspective view of the present invention. The present invention is an induced draft anti-fog system for goggles 10 and similar optical devices having an air tight goggle 12 comprising a housing 32 and lens 20 with an air intake port 24 incorporated into a hollow elastomeric air circulation conduit 22 with ends in conduit communication on opposing sides of the housing 32. The exhaust fan 26 has an on/off switch 28 in communication with two battery packs 30. When the fan 26 is in operation, air is drawn into the intake port 24 and circulated into the goggle 12, defogging the goggle lens 20 and circulated out of the fan 26.

FIG. 3 is a rear perspective view of the present invention. The present invention is an induced draft anti-fog system for goggles 10 and similar optical devices having an air tight goggle 12 comprising a housing 32 and lens 20 with an air intake port 24 incorporated into a hollow elastomeric air circulation conduit 22 with ends in conduit communication with air apertures 34 on opposing sides of the housing 32. The exhaust fan 26 has an on/off switch 28 in communication with two battery packs 30. When the fan 26 is in operation, air is drawn into the intake port 24 and circulated into the goggle 12, defogging the goggle lens 20 and circulated out of the fan 26

FIG. 4 is a frontal perspective view of the present invention. Shown is a front view of the present invention illustrating the air circulation 38 through the induced draft anti-fog system for goggles 10 and the hollow elastomeric circulation conduit 22. Air is drawn into the circulation conduit 22 through the intake port 24 by the exhaust fan 26 which is energized by the batteries 30 due to activation of the on/off switch 28. The air flow enters the housing 32 of the goggles 12 and passes of the interior surface of the lens 20 to prevent the fogging and condensation development thereof. The air returns into the circulation conduit 22 and is then expelled back into the ambient air by the exhaust fan 26. Shown is an optional barrier 36 disposed within the circulation conduit 22 to provide one-way directional air flow therethrough.

FIG. 5 is a rear perspective view of the present invention. Shown is a rear view of the present invention illustrating the air circulation 38 through the induced draft anti-fog system for goggles 10 and the hollow elastomeric circulation conduit 22. Air is drawn into the circulation conduit 22 through the intake port 24 by the exhaust fan 26 which is energized by the batteries 30 due to activation of the on/off switch 28. The air flow enters the housing 32 of the goggles 12 and passes of the interior surface of the lens 20 to prevent the fogging and condensation development thereof. The air returns into the circulation conduit 22 and is then expelled back into the ambient air by the exhaust fan 26. A hood 40 is provided for the exhaust fan 26 to protect it from damage from external entities.

FIG. 6 is a sectional view of the present invention. Shown is a sectional view of the induced draft anti-fog system for goggles 10 cut through the fan 26 and hollow air circulation conduit 22 to depict the air circulation 38 through the conduit 22 and the exhaust fan 26 during the air expulsion phase.

FIG. 7 is a sectional view of the present invention. Shown is a sectional view of the air circulation through the induced draft anti-fog system for goggles 10 cut through the air intake port 24 and circulation conduit 22 during the intake phase. Depicted is an optional filter 42 disposed within the air intake port 24 to restrict entry of dirt, debris and water into the system.

FIG. 8 is an additional element of the present invention. Shown is a rear view of the induced draft anti-fog system for goggles 10 having an additional elastic strap 44 with a plurality of loops 46, utilized as an optional attachment to the conduit 22 to allow the user to adjust the tightness of the device to one's face.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. An induced draft anti-fog device for optical lenses to prevent said lens from fogging up and accumulating condensation comprising:
   a) a goggle housing having optical lens mounted in a front wall of said housing, and an opening in said housing opposite said front wall adapted to be worn on a face of a user;

b) a first opening in one side of said housing for introducing air flow across an interior portion of said optical lens;
c) a second opening in an opposite side of said housing for removing said air flow from said interior portion of said optical lens;
d) a strap for holding said goggles to a user face extending between said first and second openings for circulating said air flow through said strap and said goggle housing;
e) comprising a battery operated exhaust fan mounted on a rear portion of said strap for circulating incoming ambient air through said housing and exhausting said ambient air after circulating through said housing;
f) an air intake port on said strap located between said exhaust fan and said first opening; and
g) a barrier member within said strap disposed between said air intake port and said exhaust fan to block any mixing of exhaust air and fresh air.

2. The induced draft anti-fog device for optical lenses according to claim 1, wherein said strap is a continuous and flexible ambient air conduit with a substantially hollow interior extending therethrough.

3. The induced draft anti-fog device for optical lenses according to claim 2, wherein said flexible conduit is in air flow communication with said first and second openings disposed on opposing sides of said goggle housing.

4. The induced draft anti-fog device for optical lenses according to claim 3, wherein said exhaust fan is energized and de-energized by said battery through activation and deactivation of an on/off switch.

5. The induced draft anti-fog device for optical lenses according to claim 4, wherein said flexible conduit is elastomeric and stretches and retracts accordingly for said housing to form a snug bond to the user's head and an airtight seal against the face thereof.

6. The induced draft anti-fog device for optical lenses according to claim 5, wherein said first opening further comprises a filter to prevent the passage of dirt, dust and debris therethrough.

7. The induced draft anti-fog device for optical lenses according to claim 6, wherein said exhaust fan includes a hood to prevent the entry of dirt and water from entering said flexible ambient air conduit.

8. The induced draft anti-fog device for optical lenses according to claim 1, wherein said strap comprises a flexible ambient air conduit mounted thereon supported by an elastic band with a plurality of loops that is adjustable to enable the user to selectively adjust the tightness of the seal of said goggle housing to their face.

9. The induced draft anti-fog device for optical lenses according to claim 1, wherein said optical lenses are selected from the group motorcycle goggles, work goggles, sports goggles and helmet face shields.

10. The induced draft anti-fog device for optical lenses according to claim 4, wherein said on/off switch is adapted to be turned on by the user thereby energizing said exhaust fan, drawing ambient air into said first opening, through said conduit and over said interior surface of said lens thereby removing fog and condensation therefrom, into the opposing side of said conduit and out through said exhaust fan.

\* \* \* \* \*